United States Patent
Herve et al.

(10) Patent No.: US 6,933,340 B2
(45) Date of Patent: Aug. 23, 2005

(54) FORMULATION COMPRISING AN IONIC COMPOUND, A POLYIONIC POLYMER, AND A BLOCK COPOLYMER

(75) Inventors: Pascal Herve, West Windsor, NJ (US); Mathias Destarac, Paris (FR); Olivier Anthony, Enghien les Bains (FR); Bruno Bavouzet, Paris (FR); Mathieu Joanicot, Chatenay-Malabry (FR); Agnieszka Zofia Wilczewska, Bialystok (PL)

(73) Assignee: Rhodia Chimie, Boulogne Billancourt (FR)

( * ) Notice: Subject to any disclaimer, the term of this patent is extended or adjusted under 35 U.S.C. 154(b) by 0 days.

(21) Appl. No.: 10/317,626

(22) Filed: Dec. 12, 2002

(65) Prior Publication Data

US 2003/0216501 A1 Nov. 20, 2003

Related U.S. Application Data

(60) Provisional application No. 60/340,886, filed on Dec. 12, 2001.

(51) Int. Cl.$^7$ .............................................. C08F 220/02
(52) U.S. Cl. ...................... 524/522; 524/556; 524/555; 524/560; 525/90; 525/94; 424/47; 424/70.16; 424/70.22; 424/70.27
(58) Field of Search ................... 525/90, 94; 524/522, 524/556, 555, 560; 424/47, 70.16, 70.22, 70.27

(56) References Cited

U.S. PATENT DOCUMENTS

| | | | | |
|---|---|---|---|---|
| 5,362,485 A | * | 11/1994 | Hayama et al. | 424/70.2 |
| 5,911,979 A | * | 6/1999 | Midha et al. | 424/70.12 |
| 6,074,628 A | * | 6/2000 | Bolich et al. | 424/47 |
| 6,093,410 A | * | 7/2000 | Peffly et al. | 424/401 |
| 6,113,883 A | * | 9/2000 | Midha et al. | 424/47 |
| 6,410,005 B1 | * | 6/2002 | Galleguillos et al. | 424/70.16 |
| 6,589,517 B1 | * | 7/2003 | McKelvey et al. | 424/70.1 |
| 6,663,855 B2 | * | 12/2003 | Frechet et al. | 424/70.11 |
| 2003/0147826 A1 | | 8/2003 | Anthony | |

FOREIGN PATENT DOCUMENTS

| WO | WO 00/02449 | 1/2000 |
|---|---|---|
| WO | WO 01/93810 | 12/2001 |

* cited by examiner

*Primary Examiner*—Tatyana Zalukaeva
*Assistant Examiner*—Satya Sastri

(57) ABSTRACT

The invention relates to a formulation comprising an ionic compound and a polyionic polymer. The invention more specifically relates to an improved formulation thereof, further comprising a copolymer. The improved formulation avoids phase-separation of colloidal particles comprising the ionic compound and the polyionic polymer. The formulation comprises a copolymer comprising two moieties A and B, wherein moiety A is polyionic in the pH conditions of the formulation, and moiety B is neutral in the pH conditions of the formulation.

20 Claims, No Drawings

FORMULATION COMPRISING AN IONIC COMPOUND, A POLYIONIC POLYMER, AND A BLOCK COPOLYMER

CROSS REFERENCES TO RELATED APPLICATIONS

This application claims the priority under 35 U.S.C. 119 and/or 365 to 60/340,886 filed in the United States on Dec. 12, 2001, the entire content of which is hereby incorporated by reference.

BACKGROUND OF THE INVENTION

The invention relates to a formulation comprising an ionic compound and a polyionic polymer. The invention more specifically relates to an improved formulation thereof, further comprising a copolymer. The improved formulation avoids phase-separation of colloidal particles comprising the ionic compound and the polyionic polymer.

A subject of the present invention is an aqueous formulation comprising a water-soluble or water-dispersible polymer, a water-soluble or water-dispersible block copolymer having at least one charged block, combined with at least one or more ionic compound having one or more charges, opposite to the charge of the block. More particularly, the said aqueous formulation is found not to precipitate nor phase-separate, but to contain stable colloidal complexes, even with a relatively small amount of block copolymers.

The block copolymer itself forms colloidal particles that do not precipitate or phase-separate when mixed with a compound having an opposite charge, such as a surfactant. The use of the block copolymer allows a joint stabilization of water-soluble polymers further comprised in a formulation within an opposite charge surfactant matrix.

The present formulation, before its use or during its use, is in the form of a colloidal suspension of opposite charge polymer-surfactant complexes with no macroscopic precipitation or phase separation.

BRIEF SUMMARY OF THE INVENTION

The invention relates to a formulation comprising:
a polymer (a), polyionic in the pH conditions of the formulation, being polycationic or polyanionic,
a compound (b), ionic in the pH conditions of the formulation,
a copolymer (c), comprising at least two moieties A and B, wherein:
  moiety A is a polyionic moiety in the pH conditions of the formulation, being polycationic if compound (b) is anionic, and polyanionic if compound (b) is cationic,
  moiety B is a neutral moiety in the pH conditions of the formulation, and
  at least one moiety selected from the group consisting of moiety A and moiety B comprises units deriving from mono-alpha-ethylenically-unsaturated monomers, and
water.

Applicants have found that copolymer (c) avoids formulation problems, for example a phase-separation, or a collapse of a suspension, of colloids or particles, in an aqueous phase, comprising the polymer (a) and the ionic compound (b). The formulations according to the invention are especially useful in cosmetics fields, and may be applied for example onto skin or onto hair. They may be used for example as hair conditioners.

A second aspect of the invention relates to a process for preparing the above-mentioned formulation.

A third aspect of the invention relates to a process for avoiding the collapse of colloidal particles in an aqueous formulation comprising:
a polymer (a), polyionic in the pH conditions of the formulation, being polycationic or polyanionic,
a compound (b), ionic in the pH conditions of the formulation,
a copolymer (c), comprising at least two moieties A and B, wherein:
  moiety A is a polyionic moiety in the pH conditions of the formulation, being polycationic if compound (b) is anionic, and polyanionic if compound (b) is cationic,
  moiety B is a neutral moiety in the pH conditions of the formulation, and
  at least one moiety selected from the group consisting of moiety A and moiety B comprises units deriving from mono-alpha-ethylenically-unsaturated monomers, and
water.

Formulations according to the third aspect are preferably cosmetics formulations, wherein polymer (a) is preferably a polycationic polymer and compound (b) is preferably an anionic compound. The process involves adding copolymer (c) to a formulation comprising polymer (a) and compound (b), preferably so as polymer (a) and copolymer (c) are combined before mixing with compound (b).

A fourth aspect of the invention relates to the use in a formulation of a copolymer (c), comprising at least two moieties A and B, wherein:
  moiety A is a polyionic moiety in the pH conditions of the formulation, being polycationic if compound (b) is anionic, and polyanionic if compound (b) is cationic,
  moiety B is a neutral moiety in the pH conditions of the formulation, and
  at least one moiety selected from the group consisting of moiety A and moiety B comprises units deriving from mono-alpha-ethylenically-unsaturated monomers,
the formulation comprising:
a polymer (a), polyionic in the pH conditions of the formulation, being polycationic or polyanionic,
a compound (b), ionic in the pH conditions of the formulation, being cationic if block A is a polyanionic block in the pH conditions of the formulation, and being anionic if block A is a polycationic block in the pH conditions of the formulation.

The use of copolymer (c) according to the fourth aspect of the invention is especially suitable in cosmetics formulations, wherein polymer (a) is a polycationic polymer, and compound (b) is an anionic compound, for example a surfactant. Such a use avoids formulation problems, for example a phase-separation, or a collapse of a suspension, of colloidal particles, in an aqueous phase, comprising polymer (a) and (b). It is for example possible to use less compound (b) in the formulation, for example less surfactant, or to formulate more polymer (a), without phase-separation or collapse.

DETAILED DESCRIPTION OF THE INVENTION

Definitions

In the present specification, the molecular weight of a polymer, a copolymer, a moiety, a graft, a side-chain, a core, a branch, a block or a backbone refers to the weight-average molecular weight of said polymer, copolymer, moiety, graft, side-chain, core, branch, block or backbone. The weight-average molecular weight of the polymer or copolymer can be measured by gel permeation chromatography (GPC). In the present specification, the molecular weight of a graft, side-chain, core, branch, block or backbone refers to the molecular weight calculated from the amounts of monomers, polymers, initiators and/or transfer agents used to make the said graft, side-chain, core, branch, block or backbone. The one skilled in the art knows how to calculate these molecular weights. The ratios by weight between moieties refer to the ratios between the amounts of the compounds used to make said moieties, considering an expensive polymerization.

Typically, the molecular weight M of a block, graft, side-chain, branch, core or backbone is calculated according to the following formula:

$$M = \sum_i M_i * \frac{n_i}{n_{precursor}},$$

wherein $M_i$ is the molecular weight of a monomer i, $n_i$ is the number of moles of a monomer i, and $n_{precursor}$ is the number of moles of a compound the macromolecular chain of the block, graft, side-chain, branch, core or backbone will be linked to. Said compound may be a transfer agent or a transfer group, a previous block, or a graft or reactive side-chain. If it is a previous block, the number of moles may be considered as the number of moles of a compound the macromolecular chain of said previous block has been linked to, for example a transfer agent or a transfer group. It may be also obtained by a calculation from a measured value of the molecular weight of said previous block. If two blocks are simultaneously grown from a previous block, at both ends, the molecular weight calculated according to the above formula should be divided by two.

In the present specification, a unit deriving from a monomer is understood as a unit that may be directly obtained from the said monomer by polymerizing. Thus, a unit deriving from an ester of acrylic or methacrylic acid does not encompass a unit of formula —CH—CH(COOH)— or —CH—C(CH$_3$)(COOH)—, obtained for example by polymerizing an ester of acrylic or methacrylic acid and then hydrolyzing. But a unit deriving from acrylic acid or methacrylic acid encompasses for example a unit obtained by polymerizing a monomer and then reacting (for example hydrolyzing) to obtain units of formula —CH—CH(COOH)— or —CH—C(CH$_3$)(COOH)—.

In the present specification the charge ratio Z, is defined as the mole ratio between the amount of charges from compound (b) and the amount of charges resulting from the algebraic sum of charges from polymer (a) and copolymer (c).

Thus, if compound (b) is anionic and polymer (a) is polycationic (moiety A being polycationic):

$$Z = \frac{\text{number of charges from compound (b)}}{\text{number of charges from polymer (a)} + \text{number of charges from copolymer (c)}} \left(\frac{(-)}{(+)}\right)$$

If compound (b) is cationic and polymer (a) is polyanionic (moiety A being polyanionic):

$$Z = \frac{\text{number of charges from compound (b)}}{\text{number of charges from polymer (a)} + \text{number of charges from copolymer (c)}} \left(\frac{(+)}{(-)}\right)$$

In the present specification, active matter is understood as the group consisting of polymer (a), compound (b), and copolymer (c). The amount of active matter is understood as the amount by weight of polymer (a), compound (b), and copolymer (c) in the formulation. The formulation may also comprise further ingredients. In the case other ingredients are also charged the definition of Z remains a charge ratio between compound (b) and same charge ingredients over the algebraic sum of charges carried by the polymer (a) and eventually copolymer (c) or same charge ingredients.

Polyionic Polymer (a)

Polymer (a) is polyionic (polyanionic or polycationic) in pH conditions of the formulation. That means that polymer (a) comprises ionic (anionic or cationic) repetitive units whatever the pH, or that polymer (a) comprises repetitive units that may be neutral or ionic (anionic or cationic) depending on the pH of the formulation (the units are potentially ionic). A unit that may be neutral or ionic (anionic or cationic), depending of the pH of the composition, will be thereafter referred as an ionic unit (anionic or cationic), or an as a unit deriving from an ionic monomer (anionic or cationic), whatever it is in a neutral form or in an ionic form (anionic or cationic).

Ionic units in polymer (a), whereas only comprised in some block(s) for block copolymer (c), are comprised all along the polymer chain, inside the chain, as side groups, or even in comb units if polymer (a) has a comb structure. It is mentioned that polymer (a) may be a statistic copolymer, comprising ionic repetitive units, and optionally neutral units, in the pH conditions of the formulation.

Examples of cationic polymers (a) include polymers comprising units deriving from monomers selected from the group consisting of:

dimethylaminoethyl (meth)acrylate, dimethylaminopropyl (meth)acrylate, ditertiobutylaminoethyl (meth)acrylate, dimethylaminomethyl (meth)acrylamide, dimethylaminopropyl (meth)acrylamide;

ethylenimine, vinylamine, 2-vinylpyridine, 4-vinylpyridine;

trimethylammonium ethyl (meth)acrylate (also called 2-(acryloxy)ethyltrimethylammonium, TMAEAMS) chloride, trimethylammonium ethyl (meth)acrylate (also called 2-(acryloxy)ethyltrimethylammonium, TMAEAMS) methyl sulphate, dimethylammonium ethyl (meth)acrylate benzyl chloride, 4-benzoylbenzyl dimethylammonium ethyl acrylate chloride, trimethyl ammonium ethyl (meth)acrylamido chloride, trimethyl ammonium propyl (meth)acrylamido chloride, vinylbenzyl trimethyl ammonium chloride, diallyldimethyl ammonium chloride, monomers having the following formula:

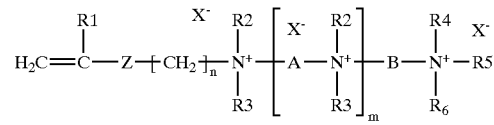

wherein $R_1$ is a hydrogen atom or a methyl or ethyl group;

$R_2$, $R_3$, $R_4$, $R_5$ and $R_6$, which are identical or different, are linear or branched $C_1$–$C_6$, preferably $C_1$–$C_4$, alkyl, hydroxyalkyl or aminoalkyl groups;

m is an integer from 1 to 10, for example 1;

n is an integer from 1 to 6, preferably 2 to 4;

Z represents a —C(O)O— or —C(O)NH— group or an oxygen atom;

A represents a $(CH_2)_p$ group, p being an integer from 1 to 6, preferably from 2 to 4;

B represents a linear or branched $C_2$–$C_{12}$, advantageously $C_3$–$C_6$, polymethylene chain optionally interrupted by one or more heteroatoms or heterogroups, in particular O or NH, and optionally substituted by one or more hydroxyl or amino groups, preferably hydroxyl groups;

X, which are identical or different, represent counterions, and their mixtures, and macromonomers deriving therefrom.

Examples of cationic polymers (a) also include cationic polymers known as precipitating onto a surface, preferably known as precipitating onto hair or skin. Mention is made of cationic polymers used in hair conditioning formulations. Examples include hydroxyalkylated ($C_2$–$C_{22}$) derivatives of cationic guars such as hydroxypropyl guar hydroxypropyl trimonium chloride (JAGUAR C162 and JAGUAR C2000 marketed by Rhodia) and cationic cellulose derivatives, in particular cellulose, 2-(2-hydroxy-3-(trimethylammonium) propoxy)ethyl ether, chloride or polyquaternium-10 (polymer JR400,Union Carbide). The cationic nature of these polymers is variable: thus in the case of cationic hydroxypropylated guar derivatives such as JAGUAR C162 and C2000 marketed by Rhodia, the degree of hydroxypropylation (molar substitution, MS), is in the range 0.02 to 1.2 and the degree of substitution, DS is in the range 0.01 to 0.6. These products can optionally be functionalised by hydrophobic groups such as alkyl chains. These cationic polymers can optionally be functionalised by anionic groups such as carboxymethyl, sulphate, sulphonate or phosphate, provided that the degree of substitution of these anionic groups is always less than the degree of substitution of the cationic groups. The molecular weight of these cationic polymers is generally at least 2000, more generally of the order of 200000 to 3000000.

Examples of anionic polymers (a) include polymers comprising units deriving from monomers selected from the group consisting of:

alpha-ethylenically-unsaturated monocarboxylic acids, such as acrylic acid and methacrylic acid, monoalkylesters of alpha-ethylenically-unsaturated dicarboxylic acids, preferably monoalkylesters of mono-alpha-ethylenically-unsaturated dicarboxylic acids, monoalkylamides of alpha-ethylenically-unsaturated dicarboxylic acids, preferably monoalkylamides of mono-alpha-ethylenically unsaturated dicarboxylic acids, alpha-ethylenically-unsaturated, preferably mono-alpha-ethylenically-unsaturated, compounds comprising a sulfonic acid group, and salts thereof, such as:

vinyl sulfonic acid, salts of vinyl sulfonic acid, vinylbenzene sulfonic acid, salts of vinylbenzene sulfonic acid, alpha-acrylamidomethylpropanesulfonic acid, salts of alpha-acrylamidomethylpropanesulfonic acid 2-sulfoethyl methacrylate, salts of 2-sulfoethyl methacrylate, acrylamido-2-methylpropanesulfonic acid (AMPS), salts of acrylamido-2-methylpropanesulfonic acid, styrenesulphonate (SS), alpha-ethylenically-unsaturated monomers comprising a phosphate or phosphonate group, and salts thereof, and their mixtures, their salts, and macromonomers deriving from therefrom.

Compound (b)

Compound (b) is an ionic compound, in the pH conditions of the formulation. In a preferred embodiment compound (b) is not a polyionic compound. That means that compound (b) does not comprise more than two electrical charges, preferably not more than one, either positive or negative.

Compound (b) include inorganic, metallic, or organic ionic compounds, either cationic or anionic.

Preferably compound (b) is anionic if polymer (a) is polycationic, and compound (b) is cationic if polymer (a) is polyanionic.

In a preferred embodiment, compound (b) is a surfactant, hereinafter mentioned as surfactant (b). Surfactant (b) is ionic in the pH conditions of the formulation (i.e. surfactant comprise at least one ionic group).

In a preferred embodiment, surfactant (b), ionic in the pH conditions of the formulation, is cationic if polymer (a) is polyanionic, and anionic if polymer (a) is polycationic.

Surfactant (b) is a cationic surfactant, in the pH conditions of the formulation, if polymer (a) is a polyanionic polymer in the pH conditions of the formulation. It is an anionic surfactant, in the pH conditions of the formulation, if polymer (a) is a polycationic polymer in the pH conditions of the formulation.

In a preferred embodiment, polymer (a) is a polycationic polymer, surfactant (b) is ionic, and moiety A is a polycationic.

The formulation according to the invention may comprise further surfactants, such as non-ionic surfactants, anionic surfactants in the pH conditions of the formulation, if polymer (a) is an anionic polymer in the pH conditions of the formulation, or cationic surfactants in the pH conditions of the formulation, if polymer (a) is a cationic polymer in the pH conditions of the formulation. These further surfactants are not understood as surfactant (b) or compound (b).

Examples of cationic surfactants (b) include the following compounds: primary, secondary or tertiary mono- or polyamines, or those possessing one or more quaternary ammonium groups, more particularly comprising 6 to 40 carbon atoms linear or branched aliphatic, aromatic, as well as those optionally comprising one or more alcoxylated ethoxylated and/or propoxylated groups. There may be cited as examples, hexylamine, octylamine, dodecylamine, stearylamine, hexadecylamine, oleylamine, diaminohexane, diaminoheptane, diaminododecane, benzoctamine, alkyldialkylammonium or alkyltrialkylammonium or alkylbenzyldialkylammonium halides, such as chloride, dodecyltrimethyl-ammonium bromide, chloride, hexadecyl-trimethylammonium bromide, chloride, benzalkonium bromide;

piperidinium salts, imidazoles, heterocyclic amines, and mixture thereof.

It is mentioned that the scope of the present invention would not be exceeded by using, on its own or in a combination with the aforementioned surfactants, one or more amphoteric surfactant, which according to the temperature and pH conditions of the composition is in a cationic form, or can develop towards such a form. It is emphasized that an amphoteric surfactant carries an anionic charge and/or a cationic charge; its degree of ionization varies according to the pH of the medium in which it is found.

As examples of such surfactants, there may be cited in particular betaines, such as in particular lauryl betaine (Mirataine BB from Rhodia); sulfo-betaines: amidoalkylbetaines, such as cocoamidopropylbetaine (Mirataine BDJ from the company Rhodia Chimie); alkylampho-acetates or -diacetates, such as cocoamphoacetates and cocoamphodiacetates (Miranol C2M, Miranol Ultra C32 from the company Rhodia Chimie), alkylamphopropionates or -dipropionates, such as Miranol C2M SF of the Rhodia Chimie company, on their own or in a mixture.

Examples of anionic surfactants (b) include the following compounds:

alkyl ester sulphonates, alkylbenzene sulphonates, primary or secondary alkylsulphonates, alkylglycerol sulphonates, sulphonated polycarboxylic acids.

alkylsulphates, sulphates of alkylglycosides, sulphated alkyl amides, alkylphosphates, the salts of saturated or unsaturated fatty acids, paraffin sulphonates, N-acyl N-alkyltaurates, isethionates, alkylsuccinamates, N-acyl sarcosinates, alkylsulfosuccinates, monoesters or diesters of sulfosuccinates, polyethoxycarboxylates.

As more precise examples of such surfactants the following can be mentioned:

Alkylester sulphonates of formula R—CH($SO_3$M)—COOR', where R represents an alkyl radical in $C_8$–$C_{20}$, preferably in $C_{10}$–$C_{16}$, R' an alkyl radical in $C_1$–$C_6$, preferably in $C_1$–$C_3$ and M an alkaline cation (sodium, potassium, lithium), substituted or non-substituted ammonium (methyl-, dimethyl-, trimethyl-, tetramethylammonium, dimethylpiperidinium . . . ) or alcanolamine derivative (monoethanolamine, diethanolamine, triethanolamine . . . ). The methyl ester sulphonates, the R radical of which is in $C_{14}$–$C_{16}$, can quite particularly be mentioned:

the alkylsulphates of formula ROS$O_3$M, where R represents an alkyl or hydroxyalkyl radical in $C_5$–$C_{24}$, preferably in $C_{10}$–$C_{18}$, M representing a hydrogen atom or a cation with the same definition as above, as well as their ethoxylated (EO) and/or propoxylated (PO) derivatives, on average having from 0.5 to 30 units, preferably from 0.5 to 10 EO and/or PO units;

the sulphated alkylamides of formula RCONHR'OS$O_3$M where R represents an alkyl radical in $C_2$–$C_{22}$, preferably in $C_6$–$C_{20}$, R' an alkyl radical in $C_2$–$C_3$, M representing a hydrogen atom or a cation of the same definition as above, as well as their ethoxylated (EO) and/or propoxylated (PO) derivatives, having on average from 0.5 to 60 EO and/or PO units;

the salts of saturated or unsaturated fatty acids in $C_8$–$C_{24}$, preferably in $C_{14}$–$C_{20}$, alkylbenzenesulphonates in $C_9$–$C_{20}$, primary or secondary alkylsulphonates in $C_8$–$C_{22}$, alkylglycerol sulphonates, sulphonated polycarboxylic acids, paraffin sulphonates, N-acyl N-alkyltaurates, alkylphosphates, isethionates, alkylsuccinamates, alkylsulfosuccinates, the monoesters or diesters, of N-acyl sulfosuccinate sarcosinates, the sulphates of alkylglycosides, polyethoxycarboxylates; the cation being an alkali metal (sodium, potassium, lithium), a substituted or non-substituted ammonium residue (methyl-, dimethyl-, trimethyl-, tetramethylammonium, dimethylpiperidinium . . . ) or alcanolamine derivative (monoethanolamine, diethanolamine, triethanolamine . . . ).

It is mentioned that the scope of the present invention would not be exceeded by using, on its own or combined with the aforementioned surfactants, an amphoteric surfactant which depending on the temperature and pH conditions of the composition are in an anionic form, or can develop into such a form. Some aforementioned amphoteric surfactants may be suitable for this embodiment, such as for example betaines, amidoalkylbetaines; alkylamphoacetates and alkylamphodiacetates; alkylamphopropionates or alkyl amphodipropionates, on their own or in a mixture.

Copolymer (c)

Copolymer (c) comprises at least two moieties, moiety A and moiety B. Copolymer (c) is a block copolymer, a star copolymer, or a grafted or comb copolymer.

Grafted or comb copolymers comprising moiety A and moiety B comprise a polymeric backbone and polymeric or oligomeric grafts or side-chains, wherein:

moiety B is the backbone and moiety A comprise the grafts or side-chains (the moiety being understood as a group of several grafts or side-chains), or moiety A is the backbone and moiety B comprise the grafts or side-chains (the moiety being understood as a group of several grafts or side-chains).

Star copolymers comprising moiety A and moiety B comprise a polymeric core and at least three polymeric branches attached to the core, wherein:

moiety B is the core and moiety A comprise the branches (the moiety being understood as several branches), or preferably, moiety A is the core and moiety B comprise the branches (the moiety being understood as several branches).

Block copolymers comprising moiety A and moiety B comprise at least two different blocks, block A, and block B. A moiety is understood as one or several blocks. Block copolymer (c) is preferably selected from the group consisting of (block A)-(block B) diblock copolymers, (block A)-(block B)-(block A) triblock copolymers, and (block B)-(block A)-(block B) triblock copolymers. The block copolymer is a linear block copolymer. By linear it is meant that the block arrangement is linear. However, a block may be a block having a comb polymer structure, that is comprising repetitive units comprising a polymeric moiety (macromonomers).

A moiety (or block) is usually defined by repeating units it comprises. A moiety (or block) may be defined by naming a polymer, or by naming monomers it derives from. In the present specification, a unit deriving from a monomer is understood as a unit that may be directly obtained from the said monomer by polymerizing. Thus, a unit deriving from an ester of acrylic or methacrylic acid does not encompass a unit of formula —CH—CH(COOH)— or —CH—C(CH$_3$)(COOH)—, obtained for example by polymerizing an ester of acrylic or methacrylic acid and then hydrolyzing. But a unit deriving from acrylic acid or methacrylic acid encompasses for example a unit obtained by polymerizing a monomer and then reacting (for example hydrolyzing) to obtain units of formula —CH—CH(COOH)— or —CH—C(CH$_3$)(COOH)—.

A moiety (or block) may be a copolymer, comprising several kind of repeating units, deriving form several monomers. Hence, moiety A (or block A) and moiety B (or block B) are different polymers, deriving from different monomers, but they may comprise some common repeating units (copolymers). Moiety A (or block A) and moiety B (or block B) preferably do not comprise more than 50% of a common repeating unit (deriving from the same monomer).

Moiety A (or block A) is a polyionic (polyanionic or polycationic) moiety (or block) in the pH conditions of the formulation. That means that moiety A (or block A) comprises ionic (anionic or cationic) units whatever the pH, or that moiety A (or block A) comprises units that may be neutral or ionic (anionic or cationic) depending on the pH of the formulation (the units are potentially ionic). A unit that may be neutral or ionic (anionic or cationic), depending on the pH of the composition, will be thereafter referred as an ionic unit (anionic or cationic), or as a unit deriving from an ionic monomer (anionic or cationic), whatever it is in a neutral form or in an ionic form (anionic or cationic). Moiety A comprises several ionic units. When moiety A is a block, a branch, a core or a backbone, said block, branch, core or backbone comprises several repetitive ionic units. When moiety A is a group of several grafts or side-chains, each graft or side chain comprise one ionic unit (the moiety comprising several ionic units because there are several grafts or side-chains), or each graft or side chain comprise several ionic units.

Moiety A (or block A) and polymer (a) are preferably alike, meaning that at least 25%, preferably 50%, of the repetitive units comprised therein are identical. They preferably essentially consist of the same units. However, their molecular weight may be different.

In a particular embodiment of the invention, moiety A (or block A) is a polycationic moiety (or block), comprising units deriving from cationic monomers.

Some preferred cationic monomers comprise an ammonium group of formula —NR$_3^+$, wherein R, which is identical or different, represents a hydrogen atom, an alkyl group comprising 1 to 10 carbon atoms, or a benzyl group, optionally carrying a hydroxyl group, and comprise an anion (counter-ion). Examples of anions are halides such as chloride and bromides, sulphates, hydrosulphates, alkylsulphates (for example comprising 1 to 6 carbon atoms), phosphates, citrates, formates, and acetates.

Examples of cationic monomers include
aminoalkyl (meth)acrylates, aminoalkyl (meth)acrylamides,
monomers, including particularly (meth)acrylates, and
 (meth)acrylamides derivatives, comprising at least one secondary, tertiary or quaternary amine function, or a heterocyclic group containing a nitrogen atom, vinylamine or ethylenimine;
diallyldialkyl ammonium salts;
their mixtures, their salts, and macromonomers deriving from therefrom.

Examples of cationic monomers include:
dimethylaminoethyl (meth)acrylate, dimethylaminopropyl (meth)acrylate, ditertiobutylaminoethyl (meth)acrylate, dimethylaminomethyl (meth)acrylamide, dimethylaminopropyl (meth)acrylamide;
ethylenimine, vinylamine, 2-vinylpyridine, 4-vinylpyridine;
trimethylammonium ethyl (meth)acrylate chloride, trimethylammonium ethyl (meth)acrylate methyl sulphate, dimethylammonium ethyl (meth)acrylate benzyl chloride, 4-benzoylbenzyl dimethylammonium ethyl acrylate chloride, trimethyl ammonium ethyl (meth)acrylamido (also called 2-(acryloxy)ethyltrimethylammonium, TMAEAMS) chloride, trimethylammonium ethyl (meth) acrylate (also called 2-(acryloxy) ethyltrimethylammonium, TMAEAMS) methyl sulphate, trimethyl ammonium propyl (meth)acrylamido chloride, vinylbenzyl trimethyl ammonium chloride,
diallyldimethyl ammonium chloride,
monomers having the following formula:

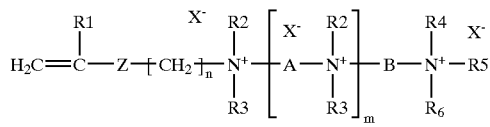

wherein
$R_1$ is a hydrogen atom or a methyl or ethyl group;
$R_2$, $R_3$, $R_4$, $R_5$ and $R_6$, which are identical or different, are linear or branched $C_1$–$C_6$, preferably $C_1$–$C_4$, alkyl, hydroxyalkyl or aminoalkyl groups;

m is an integer from 1 to 10, for example 1;
n is an integer from 1 to 6, preferably 2 to 4;
Z represents a —C(O)O— or —C(O)NH— group or an oxygen atom;
A represents a $(CH_2)_p$ group, p being an integer from 1 to 6, preferably from 2 to 4;
B represents a linear or branched $C_2$–$C_{12}$, advantageously $C_3$–$C_6$, polymethylene chain optionally interrupted by one or more heteroatoms or heterogroups, in particular O or NH, and optionally substituted by one or more hydroxyl or amino groups, preferably hydroxyl groups;
X, which are identical or different, represent counterions, and
their mixtures, and macromonomers deriving therefrom.

In a particular embodiment of the invention, moiety A (or block A) is a polyanionic moiety (or block), comprising units deriving from anionic monomers.

Examples of polyanionic moieties (or blocks) include moieties (or blocks) comprising units deriving from anionic monomers mentioned above for polymer (a) (if polymer (a) is polyanionic, or selected from the group consisting of:
alpha-ethylenically-unsaturated monomers comprising a phosphate or phosphonate group,
alpha-ethylenically-unsaturated monocarboxylic acids,
monoalkylesters of alpha-ethylenically-unsaturated dicarboxylic acids,
monoalkylamides of alpha-ethylenically-unsaturated dicarboxylic acids,
alpha-ethylenically-unsaturated compounds comprising a sulphonic acid group, and salts of alpha-ethylenically-unsaturated compounds comprising a sulphonic acid group.

Preferred polyanionic moieties (or blocks) include moieties (or blocks) comprising units deriving from at least one anionic monomer selected from the group consisting of:
acrylic acid, methacrylic acid,
vinyl sulphonic acid, salts of vinyl sulfonic acid,
vinylbenzene sulphonic acid, salts of vinylbenzene sulphonic acid,
alpha-acrylamidomethylpropanesulphonic acid, salts of alpha-acrylamidomethylpropanesulphonic acid
2-sulphoethyl methacrylate, salts of 2-sulphoethyl methacrylate,
acrylamido-2-methylpropanesulphonic acid (AMPS), salts of acrylamido-2-methylpropanesulphonic acid, and
styrenesulfonate (SS).

Moiety B (or block B) is a neutral moiety (or block) in the pH conditions of the formulation. Units comprised in moiety B (or block B) are preferably neutral whatever the pH.

Examples of neutral moieties (or blocks) include moieties (or blocks) comprising units deriving from at least one monomer selected from the group consisting of:
alkyl oxides, such as ethylene oxide, and propylene oxide,
amides of alpha-ethylenically-unsaturated, preferably mono-alpha-ethylenically-unsaturated, monocarboxylic acids, such as acrylamide, and methacrylamide,
esters of an alpha-ethylenically-unsaturated, preferably mono-alpha-ethylenically-unsaturated, monocarboxylic acid, for example alkyl esters such as such as methylacrylate, ethylacrylate, n-propylacrylate, n-butylacrylate, methylmethacrylate, ethylmethacrylate, n-propylmethacrylate, n-butylmethacrylate, 2-ethyl-hexyl acrylate, or hydroxyalkyl esters such as 2-hydroxyethylacrylate,
polyethylene and/or polyporpylene oxide (meth)acrylates (i.e. polyethoxylated and/or polypropoxylated (meth) acrylic acid), vinyl alcohol,
vinyl pyrrolidone
vinyl acetate, vinyl Versatate,
vinyl nitriles, preferably comprising from 3 to 12 carbon atoms,
acrylonitrile,
vinylamine amides,
vinyl aromatic compounds, such as styrene, and
mixtures thereof.

Moieties (or blocks) that are ionic in the pH conditions of the formulation are usually considered as water-soluble. Thus, moiety A (or block A) is usually water-soluble. In a preferred embodiment of the invention, moiety B (or block B) is also water-soluble. Water-solubility of a moiety (or block) refers to the water-solubility that said moiety (or block) would have without the other moiety (or block), that is the water-solubility of a polymer consisting of the same repeating units than said moiety (or block), having the same molecular weight. By water-soluble moiety, polymer or copolymer, it is meant that the moiety, polymer or copolymer does not phase separate macroscopically in water at a concentration of from 0, 1% and 10% by weight, at a temperature of from 20° C. to 30° C. Advantageously, copolymer (c) is water-soluble.

Neutral moiety B (or block B) may be further discriminated as regard to its hydrophilic or hydrophobic properties. Hydrophilic or hydrophobic properties of a moiety (or block) refer to the properties the moiety (or block) would have without the other moiety(ies) or (block(s)). By hydrophilic, it is meant that the moiety does not phase separate macroscopically in water at a concentration of from 0, 1% and 1% by weight, at a temperature of from 20° C. to 30° C. By hydrophobic, it is meant that the moiety does phase separate macroscopically in water at a concentration of from 0, 1% and 1% by weight, at a temperature of from 20° C. to 30° C.

Examples of neutral moieties (or blocks) considered as hydrophilic include moieties (or blocks) comprising units deriving from at least one monomer selected from the group consisting of:
ethylene oxide,
vinyl alcohol,
vinyl pyrrolidone,
acrylamide, methacrylamide,
polyethylene oxide (meth)acrylate (i.e. polyethoxylated (meth)acrylic acid),
hydroxyalkylesters of alpha-ethylenically-unsaturated, preferably mono-alpha-ethylenically-unsaturated, monocarboxylic acids, such as 2-hydroxyethylacrylate, and
hdyroxyalkylamides of alpha-ethylenically-unsaturated, preferably mono-alpha-ethylenically-unsaturated, monocarboxylic acids.

Examples of neutral moieties (or blocks) considered as hydrophobic include moieties (or blocks) comprising units deriving from at least one monomer selected from the group consisting of:
propylene oxide,
alkylesters of an alpha-ethylenically-unsaturated, preferably mono-alpha-ethylenically-unsaturated, monocarboxylic acid, such as methylacrylate, ethylacrylate, n-propylacrylate, n-butylacrylate, methylmethacrylate, ethylmethacrylate, n-propylmethacrylate, n-butylmethacrylate, and 2-ethyl-hexyl acrylate,
acrylonitrile
vinyl nitriles, comprising from 3 to 12 carbon atoms,
vinylamine amides, and
vinylaromatic compounds such as styrene.

At least one moiety selected from the group consisting of moiety A and moiety B derives from mono-alpha-ethylenically-unsaturated monomers. More precisely, it is meant that for moiety A and/or moiety B, at least 50% of the repeating units are units deriving from mono-alpha-ethylenically-unsaturated monomers. In a preferred embodiment, both moiety A and moiety B derive from mono-alpha-ethylenically-unsaturated monomers.

From the monomers mentioned above, mono-alpha-ethylenically-unsaturated monomers include:
dimethylaminoethyl (meth)acrylate, dimethylaminopropyl (meth)acrylate, ditertiobutylaminoethyl (meth)acrylate, dimethylaminomethyl (meth)acrylamide, dimethylaminopropyl (meth)acrylamide;
ethylenimine, vinylamine, 2-vinylpyridine, 4-vinylpyridine;
trimethylammonium ethyl (meth)acrylate (also called 2-(acryloxy)ethyltrimethylammonium, TMAEAMS) chloride, trimethylammonium ethyl (meth)acrylate (also called 2-(acryloxy)ethyltrimethylammonium, TMAEAMS) methyl sulphate, dimethylammonium ethyl (meth)acrylate benzyl chloride, 4-benzoylbenzyl dimethylammonium ethyl acrylate chloride, trimethyl ammonium ethyl (meth)acrylamido chloride, trimethyl ammonium propyl (meth)acrylamido chloride, vinylbenzyl trimethyl ammonium chloride,
diallyldimethyl ammonium chloride,
acrylic acid, methacrylic acid,
vinyl sulphonic acid, salts of vinyl sulfonic acid,
vinylbenzene sulphonic acid, salts of vinylbenzene sulphonic acid,
alpha-acrylamidomethylpropanesulphonic acid, salts of alpha-acrylamidomethylpropanesulphonic acid
2-sulphoethyl methacrylate, salts of 2-sulphoethyl methacrylate,
acrylamido-2-methylpropanesulphonic acid (AMPS), salts of acrylamido-2-methylpropanesulphonic acid,
styrenesulfonate (SS),
vinyl acetate,
vinyl alcohol
vinyl pyrrolidone,
styrene,
acrylamide, methacrylamide,
acrylonitrile,
methylacrylate, ethylacrylate, n-propylacrylate, n-butylacrylate, methylmethacrylate, ethylmethacrylate, n-propylmethacrylate, n-butylmethacrylate, 2-ethyl-hexyl acrylate, and
2-hydroxyethylacrylate.

There are several methods for making copolymer (c) comprising moieties A and B. In a particular embodiment, copolymer (c) is a block copolymer or a star copolymer. Some methods for making such copolymers are provided below.

It is possible for example to use anionic polymerization with sequential addition of 2 monomers as described for example by Schmolka, J. Am. Oil Chem. Soc. 1977, 54, 110; or alternatively Wilczek-Veraet et al., Macromolecules 1996, 29, 4036. Another method which can be used consists in initiating the polymerization of a block polymer at each of the ends of another block polymer as described for example by Katayose and Kataoka, Proc. Intern. Symp. Control. Rel. Bioact. Materials, 1996, 23, 899.

In the context of the present invention, it is recommended to use living or controlled polymerization as defined by Quirk and Lee (Polymer International 27, 359 (1992)). Indeed, this particular method makes it possible to prepare polymers with a narrow dispersity and in which the length and the composition of the blocks are controlled by the stoichiometry and the degree of conversion. In the context of this type of polymerization, there are more particularly recommended the copolymers which can be obtained by any so-called living or controlled polymerization method such as, for example:

free-radical polymerization controlled by xanthates according to the teaching of Application WO 98/58974 and U.S. Pat. No. 6,153,705, free-radical polymerization controlled by dithioesters according to the teaching of Application WO 98/01478, free-radical polymerization controlled by dithioesters according to the teaching of Application WO 99/35178, free-radical polymerization controlled by dithiocarbamates according to the teaching of Application WO 99/35177, free-polymerization using nitroxide precursors according to the teaching of Application WO 99/03894, free-radical polymerization controlled by dithiocarbamates according to the teaching of Application WO 99/31144, free-radical polymerization controlled by dithiocarbazates according to the teaching of Application WO 02/26836, free-radical polymerization controlled by halogenated Xanthates according to the teaching of Application WO 00/75207 and U.S. application Ser. No. 09/980,387, free-radical polymerization controlled by dithiophosphoroesters according to the teaching of Application WO 02/10223, free-radical polymerization controlled by a transfer agent in the presence of a disulphur compound according to the teaching of Application WO 02/22688, atom transfer radical polymerization (ATRP) according to the teaching of Application WO 96/30421, free-radical polymerization controlled by iniferters according to the teaching of Otu et al., Makromol. Chem. Rapid. Commun., 3,127 (1982), free-radical polymerization controlled by degenerative transfer of iodine according to the teaching of Tatemoto et al., Jap. 50. 127, 991 (1975), Daikin Kogyo Co Ltd Japan, and Matyjaszewski et al., Macromolecules, 28, 2093 (1995), group transfer polymerization according to the teaching of Webster O. W., "Group Transfer Polymerization", p. 580–588, in the "Encyclopedia of Polymer Science and Engineering", Vol. 7, edited by H. F. Mark, N. M. Bikales, C. G. Overberger and G. Menges, Wiley Interscience, New York, 1987, radical polymerization controlled by tetraphenylethane derivatives (D. Braun et al., Macromol. Symp., 111, 63 (1996)), radical polymerization controlled by organocobalt complexes (Wayland et al., J. Am. Chem. Soc., 116, 7973 (1994)).

Preferred processes are sequenced living free-radical polymerization processes, involving the use of a transfer agent. Preferred transfer agents are agents comprising a group of formula —S—C(S)—Y—, —S—C(S)—S—, or —S—P(S)—Y—, or —S—P(S)—S—, wherein Y is an atom different from sulfur, such as an oxygen atom, a nitrogen atom, and a carbon atom. They include dithioester groups, thioether-thione groups, dithiocarbamate groups, dithiphosphoroesters, dithiocarbazates, and xanthate groups.

Examples of groups comprised in preferred transfer agents include groups of formula —S—C(S)—NR—NR$'_2$, —S—C(S)—NR—N=CR$'_2$, —S—C(S)—O—R, —S—C(S)—CR=CR$'_2$, and —S—C(S)—X, wherein R and R' are or identical or different hydrogen atoms, or organic groups such as hydrocarbyl groups, optionally substituted, optionally comprising heteroatoms, and X is an halogen atom. A preferred polymerization process is a living radical polymerization using xanthates.

Copolymers obtained by a living or controlled free-radical polymerization process may comprise at least one transfer agent group at an end of the polymer chain. In particular embodiment such a group is removed or deactivated.

A "living" or "controlled" radical polymerization process used to make the block copolymers comprises the steps of:

a) reacting a mono-alpha-ethylenically-unsaturated monomer, at least a free radicals source compound, and a transfer agent, to obtain a first blocks, the transfer agent being bounded to said first block, b1) reacting the first block, another mono-alpha-ethylenically-unsaturated monomer, and, optionally, at least a radical source compound, to obtain a di-block copolymer, b2) optionally, repeating n times (n being equal to or greater than 0) step b1) to obtain a (n-2)-block copolymer, and then c) optionally, reacting the transfer agent with means to render it inactive.

For example, a "living" or "controlled" radical polymerization process used to make the di-block copolymers comprises the steps of:

a) reacting a mono-alpha-ethylenically-unsaturated monomer, at least a free radicals source compound, and a transfer agent, to obtain a first block, the transfer agent being bounded to said first block, b) reacting the first block, another mono-alpha-ethylenically-unsaturated monomer, and, optionally, at least a radical source compound, to obtain a di-block copolymer, and then c) optionally, reacting the transfer agent with means to render it inactive.

During step a), a first block of the polymer is synthesized. During step b), b1), or b2), another block of the polymer is synthesized.

Star copolymers may be prepared also by a living or controlled polymerization process involving preparing first the core and then growing branches therefrom ("core first" embodiment), or preparing first the branches and then linking the branches with a core ("arm first" embodiment.

Examples of transfer agents are transfer agents of the following formula (I):

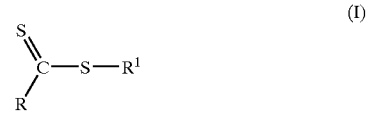

wherein:

R represents an R$^2$O—, R$^2$R$'^2$N— or R$^3$-group, R$^2$ and R$'^2$, which are identical or different, representing (i) an alkyl, acyl, aryl, alkene or alkyne group or (ii) an optionally aromatic, saturated or unsaturated carbonaceous ring or (iii) a saturated or unsaturated heterocycle, it being possible for these groups and rings (i), (ii) and (iii) to be substituted, R$^3$ representing H, Cl, an alkyl, aryl, alkene or alkyne group, an optionally substituted, saturated or unsaturated (hetero)cycle, an alkylthio, alkoxycarbonyl, aryloxycarbonyl, carboxyl, acyloxy, carbamoyl, cyano, dialkyl- or diarylphosphonato, or dialkyl- or diarylphosphinato group, or a polymer chain, $R^1$ represents (i) an optionally substituted alkyl, acyl, aryl, alkene or alkyne group or (ii) a carbonaceous ring which is saturated or unsaturated and which is optionally substituted or aromatic or (iii) an optionally substituted, saturated or unsaturated heterocycle or a polymer chain, and The $R^1$, $R^2$, $R'^2$ and $R^3$ groups can be substituted by substituted phenyl or alkyl groups, substituted aromatic groups or the following groups: oxo, alkoxycarbonyl or aryloxycarbonyl (—COOR), carboxyl (—COOH), acyloxy (—O$_2$CR), carbamoyl (—CONR$_2$), cyano (—CN), alkylcarbonyl, alkylarylcarbonyl, arylcarbonyl, arylalkylcarbonyl, isocyanato, phthalimido, maleimido, succinimido, amidino, guanidino, hydroxyl (—OH), amino (—NR$_2$), halogen, allyl, epoxy, alkoxy (—OR), S-alkyl, S-aryl or silyl, groups exhibiting a hydrophilic or ionic nature, such as alkaline salts of carboxylic acids or alkaline salts of sulphonic acid, poly(alkylene oxide) (PEO, PPO) chains, or cationic substituents (quaternary ammonium salts), R representing an alkyl or aryl group.

Preferably, the transfer agent of formula (I) is a dithiocarbonate chosen from the compounds of following formulae (IA), (IB) and (IC):

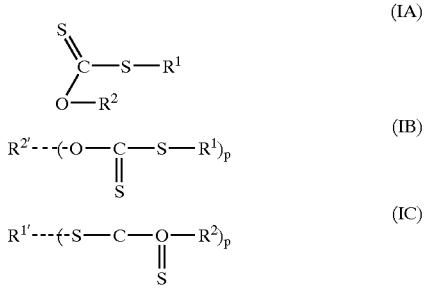

wherein:

$R^2$ and $R^{2'}$ represent (i) an alkyl, acyl, aryl, alkene or alkyne group or (ii) an optionally aromatic, saturated or unsaturated carbonaceous ring or (iii) a saturated or unsaturated heterocycle, it being possible for these groups and rings (i), (ii) and (iii) to be substituted, $R^1$ and $R^{1'}$ represent (i) an optionally substituted alkyl, acyl, aryl, alkene or alkyne group or (ii) a carbonaceous ring which is saturated or unsaturated and which is optionally substituted or aromatic or (iii) an optionally substituted, saturated or unsaturated heterocycle or a polymer chain, and p is between 2 and 10.

Other examples of transfer agents are transfer agents of the following formulae (II) and (III):

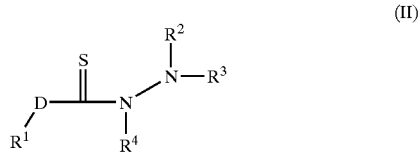

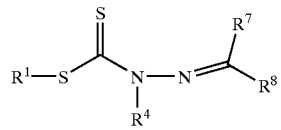

wherein $R^1$ is an organic group, for example a group $R^1$ as defined above for tranfer agents of formulae (I), (IA), (IB), and (IC), $R^2$, $R^3$, $R^4$, $R^7$, and $R^8$ which are identical or different are hydrogen atoms or organic groups, optionally forming rings. Examples of $R^2$, $R^3$, $R^4$, $R^7$, and $R^8$ organic groups include hydrocarbyls, subsituted hydrocabyls, heteroatom-containing hydrocarbyls, and substututed heteroatom-containing hydrocarbyls.

The mono-alpha-ethylenically-unsaturated monomers and their proportions are chosen in order to obtain the desire properties for the block(s). According to this process, if all the successive polymerizations are carried out in the same reactor, it is generally preferable for all the monomers used during one stage to have been consumed before the polymerization of the following stage begins, therefore before the new monomers are introduced. However, it may happen that monomers of the preceding stage are still present in the reactor during the polymerization of the following block. In this case, these monomers generally do not represent more than 5 mol % of all the monomers.

The polymerization can be carried out in an aqueous and/or organic solvent medium. The polymerization can also be carried out in a substantially neat melted form (bulk polymerization), or according to a latex type process in an aqueous medium.

The molecular weight of block copolymer (c) is preferably comprised between 1000 and 500000 g/mol. It is more preferably less than 100000 g/mol, and further more preferably between 15000 and 20000 g/mol. Within these ranges, the weight ratio of each block may vary. It is however preferred that each block have a molecular weight above 500 g/mol, and preferably above 1000 g/mol.

Process for Making the Formulation

A process for making the formulation according to the invention comprises mixing water, polymer (a), compound (b), being preferably a surfactant (b), and copolymer (c).

In a preferred embodiment, the process comprises the following steps:

i) preparing a composition comprising:
  polymer (a),
  copolymer (c), and
  water,
ii) adding compound (b), preferably a surfactant (b), into said composition to obtain a formulation, and
iii) recovering the formulation.

Structure

The formulation according to the invention is in the form of a suspension of colloids in water. It is also referred to colloidal particles. Colloids, or particles, comprise polymer (a), compound (b), and copolymer (c). Without intending to be bound to any theory, it is believe that ionic groups of polymer (a), compound (b) and copolymer (c) interact to form a complex, said complex being in the form of colloids.

Colloids in the formulation according to the invention are stable. Again, without being bound to any theory, it is believed that stabilization is due to copolymer (c), more particularly to neural moiety B. By stabilization of colloids, it is meant:

that copolymer (c) prevents a colloidal suspension comprising only polymer (a) and compound (b) to collapse or phase-separate, and/or that copolymer (c) allows the formation of a colloidal suspension in concentrations domains of water, polymer (a) and compound (b) wherein a precipitate or a dense phase would have been formed without block copolymer (c), and which would have lead to a phase-separated formulation.

Formation and stabilization of the colloidal particles may depend on the ingredients (molecular weights of polymers or copolymers, ratios (moiety B)/(moiety A) in copolymer (c), charge of polymer (a)), and on their amount in the formulation (ratios between one ingredient and the other, charge ratio Z, amount of active matter). Many parameters are at stake, that are to be appreciated by the one skilled in the art of formulating polymer (a) and/or compound (b), depending on the specifications required for the formulation, for example for an amount of active matter, an amount of surfactant, a life time of a product, and of course a cost. Some trends, or ranges of interest, are provided below:

Colloid formation occurs above a critical charge ratio $Z_c$ depending on the amount of active matter in the formulation. Z is preferably greater than 0.01, more preferably greater than 0.2.

The higher the amount of active matter is, the lower the critical charge ratio $Z_c$ is. The amount of active matter is preferably of at least 0.01% an may be of as much as 25% or even 50%.

For a given charge ratio Z, and active matter amount, the higher the ratio between moiety B and moiety A in copolymer (c), the more polymer (a) it is possible to introduce in the formulation.

For a given charge ratio Z, there is a formation of a stable colloidal dispersion at amounts of active matter that are higher than without copolymer (c). Without copolymer (c), there would be a phase separation (unstable colloids). That allows preparing highly concentrated formulations.

The use of copolymer (c) allows the formulation at as much, or more polymer (a), while using less compound (b) (for example a surfactant). In a shampoo, using as less surfactant as needed for cleaning is both cost efficient and environment friendly.

Any amount of compound (b) may be added as long as the total amount of compound (b) relative to the amount of polymer (a) and compound (c) maintains a charge ratio above the critical ratio $Z_c$. The formulation comprising colloidal complexes remains stable. It is an unexpected effect that there is a formation of colloidal complexes within a very large range of compositions (amount of active mater, ratios between polymer (a) and compound (b), charge ratio Z . . . ). Z may vary from as low as $Z_c$ to as high as 100, or even more. It can be for example of lower than 10, preferably of lower than 7.5, preferably of lower than 5, preferably of lower than 2.5 or even of lower than or equal to 1.

For example, a hair care and/or skin care formulation according to the invention may comprise an amount of polymer (a) (preferably cationic) of from 0.1 to 1% by weight, with an amount of surfactant (b) (preferably anionic) of lower than 10% (Z being preferably of lower than 10), or even of lower than 7.5% (Z being preferably of lower than 7.5), or even of lower than 5 or 2.5% (Z being preferably of lower than 5 or 2.5).

It is mentioned that formulation according to the invention may comprise some other ingredients. They may for example comprise ingredients used in cosmetic compositions, preferably in hair care and/or skin care formulations, such as a hair-conditioning formulation.

EXAMPLES

Concrete but non-limiting examples of the invention are presented below.

Example 1

The subject of this example is the preparation of a homogeneous and stable monophasic composition containing an anionic polymer (polyelectrolyte), a cationic surfactant, and an anionic-neutral diblock copolymer.

The polyelectrolyte is the sodium salt of a polyacrylic acid, the cationic surfactant is the dodecyltrimethylammoniumbromide (DTAB), and the anionic-neutral diblock copolymer is made up of a polyacrylic acid first block (Mw=5,000 g/mole) and a polyacrylamide second block (Mw=30,000 g/mole) noted $PAA_{5k}$-b-$PAM_{30k}$.

1/ Synthesis of the Anionic-Neutral Diblock Copolymer: $PAA_{5k}$-$PAM_{30k}$

It is carried out according to a batch process, at 70° C., in a double-jacketed reactor.

First Stage: $PAA_{5k}$-X Synthesis

Acrylic acid, water, S-ethylpropionyl O-ethyl xanthate and isopropanol are introduced as a starter, with 4,4-azo-bis-4-cyanovaleric acid or ACP (50% relative to the xanthate functions). The mixture is thus heated for 6 hours to 70° C.

| Mass of the reagents introduced | | | | |
| --- | --- | --- | --- | --- |
| Acrylic acid | Water | Xanthate | Isopropanol | ACP |
| 7.7 g | 16.7 g | 0.32 g | 2.5 g | 0.2158 g |

Second Stage: $PAA_{5k}$-$PAM_{30k}$ Synthesis

Acrylamide, dissolved in the water and the ACP (50% relative to the xanthate functions) is added to the previous mixture which is again heated for 6 hours to 70° C.

| Mass of the reagents introduced | | |
| --- | --- | --- |
| Acrylamide | Water | ACP |
| 46.2 g | 109.8 g | 0.2158 g |

The concentration of the final solution is 34 wt. % measured by moisture analyser.

2/ Formation of Colloidal Complexes Containing an Anionic Polyelectrolyte. Solution 1A:

The previously obtained diblock copolymer solution is neutralised with Sodium Hydroxide (1 equivalent per acid group), then diluted with water to obtain a final active level of 5 wt. %.

Solution 1B:

A 5 wt. % solution of Sodium Polyacrylate homopolymer is prepared by diluting a 40 wt. % solution in water of Poly(acrylic Acid, Sodium Salt) from Aldrich (Average Mw ca. 30,000)[CAS# 9003-04-7].

Solution 1C:

A mixture of the two solutions 1A and 1B is prepared in order to have 90% of acrylate groups belonging to the Homopolymer.

Solution 1D:

This resulting mixed 5 wt. % solution 1C is then further mixed with an aqueous 5 wt. % solution of cationic surfactant DTAB (Dodecyl Trimethyl Ammonium Bromide, Fluka) in such a way that the molar ratio of the totality of the cationic charges to the totality of the anionic charges, $Z=[+]/[-]$ equals 1.

The resulting solution 1D contains stable well defined colloids. The size of the colloidal complexes measured by dynamic light scattering is 130 nm.

Example 2

The subject of this example is the preparation of a homogeneous and stable monophasic composition containing a cationic polymer (polyelectrolyte), an anionic surfactant, and a cationic-neutral diblock copolymer.

The cationic polyelectrolyte is the methylsulfate [2-(acryloyloxy)ethyl]-trimethylammonium homopolymer (polyTMAEAMS), the anionic surfactant the sodium sodecyl sulfate, and the cationic-neutral diblock copolymer is made up of a polyTMAEAMS first block (Mw=11,000 g/mole) and a polyacrylamide second block (Mw=30,000 g/mole) noted polyTMAEAMS$_{11k}$-b-polyAM$_{30k}$.

1/ Synthesis of a Diblock Copolymer polyTMAEAMS-b-polyAM 11K–30K

The synthesis is carried out according to a batch process, at 70° C., in a double jacketed reactor.

First Stage: polyTMAEAMS$_{11k}$-X synthesis

The solution of [2-(acryloyloxy)ethyl]-trimethylammonium methyl sulfate (TMAEAMS) and water are introduced in the reactor and the solution is heated to 70° C. Then a mixture of S-ethylpropionyl O-ethyl xanthate, 4,4'-azo-bis-4-cyanovaleric acid or ACVA (30 mole % relative to the xanthate) and isopropanol is introduced. The obtained mixture is stirred overnight at 70° C.

| Mass of the reagents introduced | | | | |
|---|---|---|---|---|
| TMAEAMS (80 w % in water) | Water | Xanthate | ACVA | Isopropanol |
| 6.69 g | 8.92 g | 0.103 g | 0.042 g | 1.75 g |

Second stage: polyTMAEAMS$_{11k}$-PAM$_{30k}$ synthesis

The ACVA (50 mole % relative to the xanthate) dissolved in the water is added to the previous mixture.

| Mass of the reagents introduced | |
|---|---|
| ACVA | Water |
| 0.07 g | 26.28 g |

The acrylamide dissolved in the water (I) is then added continuously during 3 hours. After the first hour, the ACVA (22 mole % relative to the xanthate) dissolved in the water (II) is added.

| Mass of the reagents introduced | | | |
|---|---|---|---|
| Acrylamide | Water (I) | ACVA | Water (II) |
| 14.6 g | 41.5 g | 0.03 g | 0.05 g |

After the second hour, the ACVA (22 mole % relative to the xanthate) dissolved in the water is added.

| Mass of the reagents introduced | |
|---|---|
| ACVA | Water |
| 0.03 g | 0.05 g |

After the three hours, the mixture is again stirred at 70° C. for two hours.

The dry extract of the final solution is 20%.

2/ Formation of Colloidal Complexes with Homopolymer

Solution 2A:

The previously obtained diblock copolymer solution is brought to neutral pH with Sodium Hydroxide to compensate any slight excess of Methyl Sulfate, and is then diluted with water to obtain a final active level of 5 wt %.

Solution 2B:

A 5 wt. % solution of [2-(acryloyloxy)ethyl]-trimethylammonium methyl sulfate (TMAEAMS) homopolymer is prepared by diluting a 20 wt. % solution obtained following the same synthesis as described above for the first cationic block (Average Mw=11,000 g/mole). The pH of this solution was also fixed to neutrality.

Solution 2C:

A mixture of the two solutions 2A and 2B is prepared in order to have 90% of TMAEAMS groups belonging to the Homopolymer.

Solution 2D:

This resulting mixed 5 wt. % solution 2C is then further mixed with an aqueous 5 wt. % solution of anionic surfactant SDS (Sodium Dodecyl Sulfate, Fluka) in such a way that the molar ratio of the totality of the anionic charges to the totality of the cationic charges, $Z=[-]/[+]$ equals 1.

The resulting solution contains stable light scattering colloids

Example 3

The subject of this example is the preparation of a homogeneous and stable monophasic composition containing an anionic polymer (polyelectrolyte), a cationic surfactant, and an anionic-neutral diblock copolymer.

The polyelectrolyte is the sodium salt of a polystyrene sulfonic acid, the cationic surfactant is the dodecyl trimethyl ammonium bromide (DTAB), and the anionic-neutral diblock copolymer is made up of a polystyrene sulfonic acid first block (Mw=5,000 g/mole) and a polyacrylamide second block (Mw=30,000 g/mole) noted PSS$_{5k}$-b-PAM$_{30k}$.

1/ Synthesis of the Anionic-Neutral Diblock Copolymer: PSS$_{5k}$-PAM$_{30k}$

It is carried out according to a batch process, at 70° C., in a double-jacketed reactor.

First Stage: PSS$_{5k}$-X Synthesis

Stryrene sulfonic acid, Water/Ethylene Glycol (80/20), and S-ethylpropionyl O-ethyl xanthate are introduced as a starter, with 4,4-azo-bis-4-cyanovaleric acid or ACP (50% relative to the xanthate functions). The mixture is thus heated for 24 hours to 70° C. The Polystyrene sufonate is precipitated in acetonitrile.

| Mass of the reagents introduced | | | | |
|---|---|---|---|---|
| Styrene Sulfonic acid | Water | Xanthate | Ethylene Glycol | ACP |
| 7.7 g | 16.7 g | 0.32 g | 4.2 g | 0.2158 g |

Second stage: $PSS_{5k}$-$PAM_{30k}$ Synthesis

The acrylamide, dissolved in the water and the ACP (50% relative to the xanthate functions) are added to the previous block redissolved in 21 g of water and is again heated for 6 hours to 70° C.

| Mass of the reagents introduced | | |
|---|---|---|
| Acrylamide | Water | ACP |
| 46.2 g | 109.8 g | 0.2158 g |

The concentration of the final solution is 28.8 wt. % measured by moisture analyser.

2/ Formation of Colloidal Complexes Containing an Anionic Polyelectrolyte.

Solution 3A:

The previously obtained diblock copolymer solution is neutralised with Sodium Hydroxide (1 equivalent per acid group), then diluted with water to obtain a final active level of 5 wt. %.

Solution 3B:

A 5 wt. % water solution of Poly(Sodium 4-styrenesulfonate) is prepared (homopolymer from Aldrich (Average Mw ca. 70,000)[CAS # 25704-18-1]).

Solution 3C:

A mixture of the two solutions 3A and 3B is prepared in order to have 70% of Styrene sulfonate groups belonging to the homopolymer.

Solution 3D:

This resulting mixed 5 wt. % solution 3C is then further mixed with an aqueous 5 wt. % solution of cationic surfactant DTAB (Dodecyl Trimethyl Ammonium Bromide, Fluka) in such a way that the molar ratio of the totality of the cationic charges to the totality of the anionic charges, $Z=[+]/[-]$ equals 1.

The resulting solution 3D contains stable well defined colloids. The size of the colloidal complexes measured by dynamic light scattering is 130 nm.

Example 4

The subject of this example is the preparation of a homogeneous and stable monophasic composition containing an anionic polymer (polyelectrolyte), a cationic surfactant, and an anionic-neutral diblock copolymer.

The polyelectrolyte is the sodium salt of a poly(2-acrylamido-2-methylpropanesulfonic acid, the cationic surfactant is the dodecyl trimethyl ammonium bromide (DTAB), and the anionic-neutral diblock copolymer is made up of a poly(2-acrylamido-2-methylpropanesulfonic Acid) acid first block (Mw=5,000 g/mole) and a polyacrylamide second block (Mw=30,000 g/mole) noted $PAMPS_{5k}$-b-$PAM_{30k}$.

1/ Synthesis of the Anionic-Neutral Diblock Copolymer: $PAMPS_{5k}$-$PAM_{30k}$

It is carried out according to a batch process, at 70° C., in a double-jacketed reactor.

First Stage: $PAMPS_{5k}$-X synthesis 2-acrylamido-2-methylpropanesulfonic Acid, water, S-ethylpropionyl O-ethyl xanthate and isopropanol are introduced as a starter, with 4,4-azo-bis-4-cyanovaleric acid or ACP (50% relative to the xanthate functions). The mixture is thus heated for 6 hours to 70° C.

| Mass of the reagents introduced | | | | |
|---|---|---|---|---|
| AMPS | Water | Xanthate | Isopropanol | ACP |
| 7.7 g | 16.7 g | 0.32 g | 2.5 g | 0.2158 g |

Second stage: $PAMPS_{5k}$-$PAM_{30k}$ synthesis

The acrylamide, dissolved in the water and the ACP (50% relative to the xanthate functions) are added to the previous mixture and is again heated for 6 hours to 70° C.

| Mass of the reagents introduced | | |
|---|---|---|
| Acrylamide | Water | ACP |
| 46.2 g | 109.8 g | 0.2158 g |

The concentration of the final solution is 40 wt. % measured by moisture analyser.

2/ Formation of Colloidal Complexes Containing an Anionic Polyelectrolyte.

Solution 4A:

The previously obtained diblock copolymer solution is neutralised with Sodium Hydroxide (1 equivalent per acid group), then diluted with water to obtain a final active level of 5 wt. %.

Solution 4B:

A 5 wt. % solution of Sodium Poly(2-acrylamido-2-methylpropane sulfonic Acid) homopolymer is prepared by diluting a 20 wt. % solution in water of poly 2-acrylamido-2-methylpropanesulfonic Acid from Rhodia, Inc. and neutralizing it with hodium hydroxide (The homopolymer was synthetise by Rhodia, Inc. using a standard radical polymerization in a batch process with Sodium Persulfate as an initiator at 0.01% with respect to the monomer at 60 deg.C. in water for two hours (Viscosity at 20% active=20 000 cPs on a Brookfield spindle $N^O4$ @12 rpm)).

Solution 4C:

A mixture of the two solutions 4A and 4B is prepared in order to have 60% of 2-acrylamido-2-methylpropanesulfonate groups belonging to the Homopolymer.

Solution 4D:

This resulting mixed 5 wt. % solution 4C is then further mixed with an aqueous 5 wt. % solution of cationic surfactant DTAB (Dodecyl Trimethyl Ammonium Bromide, Fluka) in such a way that the molar ratio of the totality of the cationic charges to the totality of the anionic charges, $Z=[+]/[-]$ equals 1.

The resulting solution 4D contains stable well defined colloids. The size of the colloidal complexes measured by dynamic light scattering is 150.

What is claimed is:

1. A formulation comprising:
   a polymer (a), polyionic in the pH conditions of the formulation, being polycationic or polyanionic,
   a compound (b), ionic in the pH conditions of the formulation,
   a copolymer (c), comprising at least two moieties A and B, wherein:
   moiety A is a polyionic moiety in the pH conditions of the formulation, being polycationic if compound (b) is anionic, and polyanionic if compound (b) is cationic,
   moiety B is a neutral moiety in the pH conditions of the formulation, and
   at least one moiety selected from the group consisting of moiety A and moiety B comprises units deriving from mono-alpha-ethylenically-unsaturated monomers, and
   water,
   wherein B is a hydrophilic water-soluble block.

2. A formulation according to claim 1, wherein block B comprises units deriving from monomers selected from the group consisting of:
   ehtylene oxide,
   vinyl alcohol,
   vinyl pyrrolidone,
   polyethylene oxide (meth)acrylate (i.e. polyethoxylated (meth)acrylic acid),
   hydroxyalkylesters of alpha-ethylenically-unsaturated, monocarboxylic acids,
   hydroxyalkylamides of alpha-ethylenically-unsaturated monocarboxylic acids,
   acrylamide, and methacrylamide.

3. The formulation according to claim 1, wherein compound (b) is a surfacant.

4. The formulation according to claim 1, wherein compound (b) is anionic if polymer (a) is polycationic, and compound (b) if cationic if polymer (a) is polyanionic.

5. The formulation according to claim 3, wherein surfacant (b), ionic in the pH conditions of the formulation, is cationic if polymer (a) is polyanionic, and anionic if polymer (a) is polycationic.

6. The formulation according to claim 3, wherein polymer (a) is polycationic, surfacant (b) is anionic, and block A is polycationic.

7. The formulation according to claim 1, wherein polymer (a) comprises repeating units, block A comprises repeating units, and at least 25% by weight of the repeating units of polymer (a) are identical to at least 25% by weight of the repeating units of block A.

8. The formulation according to claim 7, wherein polymer (a) and block A essentially consists of the same repeating units.

9. The formulation according to claim 1, wherein polymer (a) comprises more than 10 ions in the pH conditions of the formulation.

10. The formulation according to claim 1, wherein the block coploymer (c) is a di-block (block A)-(block B) copolymer, a tri-block (block A)-(block B)-(block A) copolymer, or a tri-block (block B)-(block A)-(block B) copolymer.

11. The formulation according to claim 10, wherein block A and block B comprise repeating units deriving from mono-alpha-ethylenically-unsaturated monomers.

12. The formulation according to claim 1, wherein block A is a polycationic block and comprises repeating units deriving from monomers selected from the group consisting of:
   dimethylaminethyl (meth)acrylate, dimethaminopropyl (meth)acrylate, ditertiobutlaminoethyl (meth)acrylate, dimethlaminomethyl (meth)acrylamide, dimethylaminoproply (meth)acrylamide;
   ethylenimine, vinylamine, 2-vinylpyridine, 4-vinylpyridine;
   trimehylammonium ethyl (meth)acrylate chloride, trimethylammonium ehtyl (meth)acrylate methyl sulphate, dimethylammonium ethyl (meth)acrylate benzyl chloride, 4-benzoylbenzyl dimethylammonium ethyl acrylate chloride, trimethyl ammonium ethyl (meth) acrylamido chloride, trimethyl ammonium propyl (meth)acrylamido chloride, vinylbenzyl trimethyl ammonium chloride,
   diallyldimethyl ammonium chloride,
   their mixtures, and macromonomers deriving therefrom.

13. The formulation according to claim 1, wherein block A is a polyanionic block and comprises repeating units deriving from monomers selected from the group consisting of:
   alpha ethylenically unsaturated monomers comprising a phosphate or phosphonate group,
   alpha ethylenically unsaturated monocarboxylic acids,
   monoalkylesters of alpha ethylenically unsaturated dicarboxyic acids,
   monoalkylamides of alpha ethylenically unsaturated dicarboxyic acids,
   alpha ethylenically unsaturated compounds comprising a sulphonic acid group, and salts of alpha ethylenically unsaturated compounds comprising a sulphonic acid group.

14. The formulation according to claim 1, wherein block A is a polynaionic block and comprises repeating units deriving from monomers selected from the group consisting of:
   acrylic acid, methacrylic acid,
   vinyl sulphonic acid, salts of vinyl sulfonic acid,
   vinylbenzene sulphonic acid, salts of vinylbenzene sulphonic acid,
   alpha-acrylamidomethylpropanesulphonic acid, salts of alpha-acrylamidomethylpropanesulphonic acid
   2-sulphoethyl methacrylate, salts of 2-sulphonethyl methacrylate,
   acrylamido-2-methylpropanesulphonic acid (AMPS), salts of acrylamido-2-methylpropanesulphonic acid; and
   styrenesulphonate (SS).

15. The formulation according to claim 1, wherein the block copolymer (c) is obtained by a living or controlled free-radical polymerization process.

16. The formulation according to claim 1, further comprising ingredients of a cosmetic composition.

17. The formulation according to claim 16, wherein the cosmetic composition comprises ingredients of a composition to be used on skin.

18. The formulation according to claim 16, wherein the cosmetic composition comprises ingredients of a composition to be used on hair.

19. The formulation according to claim 18, wherein the composition is a hair-conditioning composition.

20. The formulation according to claim 1, being in the form of a suspension of colloids in water, said colloids comprising polymer (a), compound (b), and copolymer (c).

* * * * *